US011158428B1

(12) United States Patent
Siegel et al.

(10) Patent No.: US 11,158,428 B1
(45) Date of Patent: Oct. 26, 2021

(54) SYSTEM AND METHOD FOR COMMUNICATING PREDICTED MEDICAL OUTCOMES

(71) Applicant: Dartmouth-Hitchcock Clinic, Lebanon, NH (US)

(72) Inventors: Corey A. Siegel, Hanover, NH (US); Lori S. Siegel, Hanover, NH (US); Marla C. Dubinsky, Los Angeles, CA (US)

(73) Assignee: MiTest Health LLC, Dover, DE (US)

( * ) Notice: Subject to any disclaimer, the term of this patent is extended or adjusted under 35 U.S.C. 154(b) by 820 days.

(21) Appl. No.: 14/589,980

(22) Filed: Jan. 5, 2015

Related U.S. Application Data (63) Continuation of application No. 12/731,131, filed on Mar. 24, 2010, now abandoned.

(60) Provisional application No. 61/163,024, filed on Mar. 24, 2009.

(51) Int. Cl.
*G16H 50/50* (2018.01)
*G16H 50/30* (2018.01)

(52) U.S. Cl.
CPC ............. *G16H 50/50* (2018.01); *G16H 50/30* (2018.01)

(58) Field of Classification Search
CPC .. G06F 19/3437; G06F 19/3431; G16H 50/50
See application file for complete search history.

(56) References Cited

U.S. PATENT DOCUMENTS

| 7,805,385 | B2 * | 9/2010 | Steck ............... G06F 19/345 706/10 |
|---|---|---|---|
| 2005/0032066 | A1 | 2/2005 | Heng et al. |
| 2005/0125158 | A1 | 6/2005 | Schlessinger et al. |
| 2005/0203773 | A1 | 9/2005 | Soto et al. |
| 2009/0326976 | A1 | 12/2009 | Morris |
| 2010/0198571 | A1 | 8/2010 | Morris et al. |

OTHER PUBLICATIONS

Fox, "Cox Proportional-Hazards Regression for Survival Data", "An R and S-PLUS Companion to Applied Regression", Feb. 2002.
(Continued)

*Primary Examiner* — Sheetal R Paulson
(74) *Attorney, Agent, or Firm* — Loginov & Associates, PLLC; William A. Loginov (57) ABSTRACT

A system and method for predicting medical outcomes of patients having a variety of diseases, and communicating these predicted outcomes to the patients. The system and method incorporates a plurality of variables and available medical treatments and/or therapies that are available to a patient. All of the variables and treatments are analyzed to predict medical outcomes without treatment, and with each of the plurality of available treatments. The system includes a graphical user interface for inputting the variables and the treatment options. This graphical user interface can comprise a plurality of toggle switches for manipulating each variable as desired. The graphical user interface can display a risk of complication of a disease, both with and without treatment, to a patient, thereby improving communication to the patient and providing healthcare providers and professionals with a procedure and system by which medical outcomes may be predicted and readily communicated to patient.

16 Claims, 9 Drawing Sheets

(56) References Cited

OTHER PUBLICATIONS

University of Maryland Medical Center, "Crohn's Disease—Complications", "http://www.umm.edu/patiented/articles/how_serious_crohns_disease_000103_4.htm", Dec. 1, 2008, Publisher: University of Maryland Medical Center.

Chan, et al., "Incremental Benefit and Cost-Effectiveness of High-Dose Statin Therapy in High-Risk Patients With Coronary Artery Disease", "Circulation", Apr. 23, 2007, pp. 2398-2409, vol. 115, Publisher: American Heart Association.

Mackenzie, et al., "Prediction of Survival After Coronary Revascularization: Modeling Short-Term, Mid-Term, and Long-Term Survival", "Ann Thorac Surg", Sep. 16, 2008, pp. 463-474, vol. 2009, No. 87, Publisher: The Society of Thoracic Surgeons.

Eagle, et al., "A Validated Prediction Model for All Forms of Acute Coronary Syndrome", "JAMA", Jun. 9, 2004, pp. 2727-2733, vol. 291, No. 22, Publisher: American Medical Association.

WebMD Health News, "You Can Predict Your Newborn's Weight", "http://www.webmd.com/baby/news/20020926/you-can-predict-your-newborns-weight", Sep. 26, 2002, Publisher: WebMD Health News.

\* cited by examiner

SYSTEM AND METHOD FOR COMMUNICATING PREDICTED MEDICAL OUTCOMES

RELATED APPLICATIONS

This application is a continuation of co-pending U.S. patent application Ser. No. 12/731,131, filed Mar. 24, 2010, entitled SYSTEM AND METHOD FOR COMMUNICATING PREDICTED MEDICAL OUTCOMES, which claims the benefit of U.S. Provisional Application Ser. No. 61/163,024, filed Mar. 24, 2009, entitled SYSTEM AND METHOD FOR COMMUNICATING PREDICTED MEDICAL OUTCOMES TO PATIENTS, the entire disclosure of each which applications is herein incorporated by reference.

STATEMENT REGARDING FEDERALLY SPONSORED RESEARCH OR DEVELOPMENT

This invention was made with U.S. government support under Grant Numbers DK078678 and DK066248, awarded by the National Institutes of Health. The government may have certain rights in this invention.

FIELD OF THE INVENTION

The present invention relates to systems and methods for communicating predicted medical outcomes.

BACKGROUND OF THE INVENTION

Unfortunately, there are a number of medical illnesses, or other medical conditions, affecting patients for which the preferred method of treatment has not yet been determined and/or the factors affecting the medical condition are not readily communicated. Each medical illness generally has several treatment options for reducing a patient's risk of developing complications of their disease and thereby improving their long-term quality of life. These risks can vary depending on the particular treatment and patient being treated. Accordingly, these risks affect the decision of physicians, patients and their families on whether or not to administer a treatment and which treatment, if any, to administer to patient.

Likewise, there are several conditions that are affected by a person's behaviors, actions or other factors, which can cause an impact. Other than to verbally communicate the various factors and associated risks and effects of the factors, there is no effective mechanism for communicating the affects on a medical condition.

However, there is not yet available a system and method that communicates the potential risks of a disease, the risks associated with each available treatment, and the expected benefits of therapy. According to available systems, a doctor can only verbally communicate to the patient and/or the patient's family the individualized risks of their disease and risks and benefits associated with each medical treatment, as well as the risks and benefits associated with a particular variable (i.e. smoking, and the affect it has on your risk of a heart attack). Accordingly, due to this uncertain disease course, apprehension over side-effects, and concern of "over treating" the disease, among other factors, treatment is often undesirably delayed.

It is thus desirable to provide a system and method for effectively communicating individualized information to patients, families and consulting physicians. It is also desirable to provide a system and method for predicting medical outcomes of various diseases. More desirably, a system should further determine the risk of complication of the disease, based on various treatments available, as well as based on a particular variable or contributing factor.

Even more desirably, a system should further display the risk of complication of disease to a patient, to effectively and efficiently communicate the disease risk or medical outcome to a patient or other physician. It is desirable to be able to manipulate the system so as to provide patient-specific precise predictions.

SUMMARY OF THE INVENTION

This invention overcomes disadvantages of the prior art by providing a system and method that employs a procedure for communicated predicted medical outcomes to a patient, physician or clinician in a medical environment. The procedure provides a precise prediction for an outcome of interest with respect to a medical condition for one of any number of diseases, medical conditions or outcome(s) of interest. For example, providing a precise predicted birth weight of a baby in response to a number of variables, such as whether or not the mother smokes, her diet during pregnancy, and other contributing variables, are provided in accordance with an illustrative embodiment.

The system and method incorporates a plurality of patient-specific variables and related data, and can further input a plurality of medical treatments or therapies available to a patient. All of the variable and treatments are analyzed to predict an outcome of interest and provide a model for a computational engine which generates a predicted outcome. The computational engine allows clinicians to manipulate the variables to determine their effect on the outcome of interest. The outcome of interest can be displayed graphically both without any treatment, and with each of a plurality of available treatments to reflect the risk of an outcome of interest for the various possible scenarios.

In an illustrative embodiment, the variables are entered into the system to predict medical outcomes, and can include gender, age at diagnosis (or onset of a medical condition), months since diagnosis, medical condition characteristics, behavioral factors, environmental factors, genetic testing and other blood tests. Treatment options can include, for example in the case of Crohn's disease, prednisone, immunomodulators, anti-tumor necrosis factor agents, and natalizumab. For Rheumatoid Arthritis, treatment options are similar and also include prednisone, immunomodulators and anti-TNF agents.

The system includes a graphical user interface (GUI) for inputting the variables and including available treatment options. This GUI can comprise a plurality of switches for changing each variable as desired, thereby reflecting the effect each variable has on the outcome of interest. The graphical user interface can display a risk of complication of a disease, both with and without treatment, to a patient. The GUI can also be used to display the outcome of interest for a particular medical condition for which treatment is not required, such as for a predicted birth weight, and a patient or clinician can observe the effects of each factor on the predicted birth weight. This arrangement improves communication to the patient and advantageously provides healthcare providers and professionals with a means by which medical outcomes can be predicted and readily communicated to patients.

An illustrative procedure of prediction initiates with the step of inputting the medical condition to be analyzed and/or treated. This provides the relevant input variables associated with the medical condition. According to the procedure, the outcome(s) of interest are determined, for which the prediction occurs, such as the predicted birth weight or a likelihood of a heart attack. Functional relationships are then built based upon the medical condition and outcome of interest. This includes clinical verification of the functional relationships based upon established precedence in the medical profession, and to remove biased or confounded input variables. Next, based upon accurate functional relationships, the system model is developed for the computational engine which accepts input variables and provides a predicted outcome.

Once a valid model exists for the computational engine, the predicted outcome is output as a graphical representation. The graphical representation provides a predicted medical outcome and/or a risk of complication of a medical condition, over time. This is displayed without treatment in an illustrative embodiment to show the risk of complication if no treatment is performed. For patients in which treatment is not required (i.e. his or her risk of complication is low, or the medical condition being analyzed is not subject to treatment), no further steps are performed. For patients having a high risk of disease complication, one of a plurality of available treatment options is also input into the computational engine. This variable further affects the risk of complication, or outcome of interest, and is determined by the computational engine, which thus outputs a graphical display of the risk of complication both with and without treatment. This can be repeated for each available treatment to assist patients and healthcare providers in determining appropriate treatment options.

BRIEF DESCRIPTION OF THE DRAWINGS

The invention description below refers to the accompanying drawings, of which.

DETAILED DESCRIPTION

In accordance with an illustrative embodiment there is provided a system and method for communicating predicted medical outcome(s) of interest and associated treatments to patients. There are a number of variables that each, in a different way, affects medical outcomes. Medical outcomes are also affected by various treatments, depending on the type of treatment. This can be used as a medical prediction tool for a variety of applications, diseases, conditions, or predictable states, to verify the effects, benefits or risks of a particular variable of a medical treatment.

A plurality of data variables are analyzed by the various components of the system, including electronic devices and operators of the devices. The medical outcomes for patients can thereby be predicted and communicated to a patient, doctor, clinician, or other interested individual by building a system model for a computational engine. The computational engine refers to a runtime engine instantiated on a computing system that operates upon a plurality of data variables and mathematical associations or functions to compute and display a predicted outcome. The computational engine can be, in whole or part, provided by an existing software platform that computes or displays, or computes and displays, the predicted outcome. Also, a custom built computational engine can be substituted or an alternate computational engine can be employed. A person of ordinary skill can create the computational engine such that input variables are used to create a desired visual output, based on known established relationships. This provides physicians and clinicians with a runtime tool for reviewing the various outcome(s) of interest and the effects various variables have on the outcome(s), including input variables and medical treatments.

Figure 1:
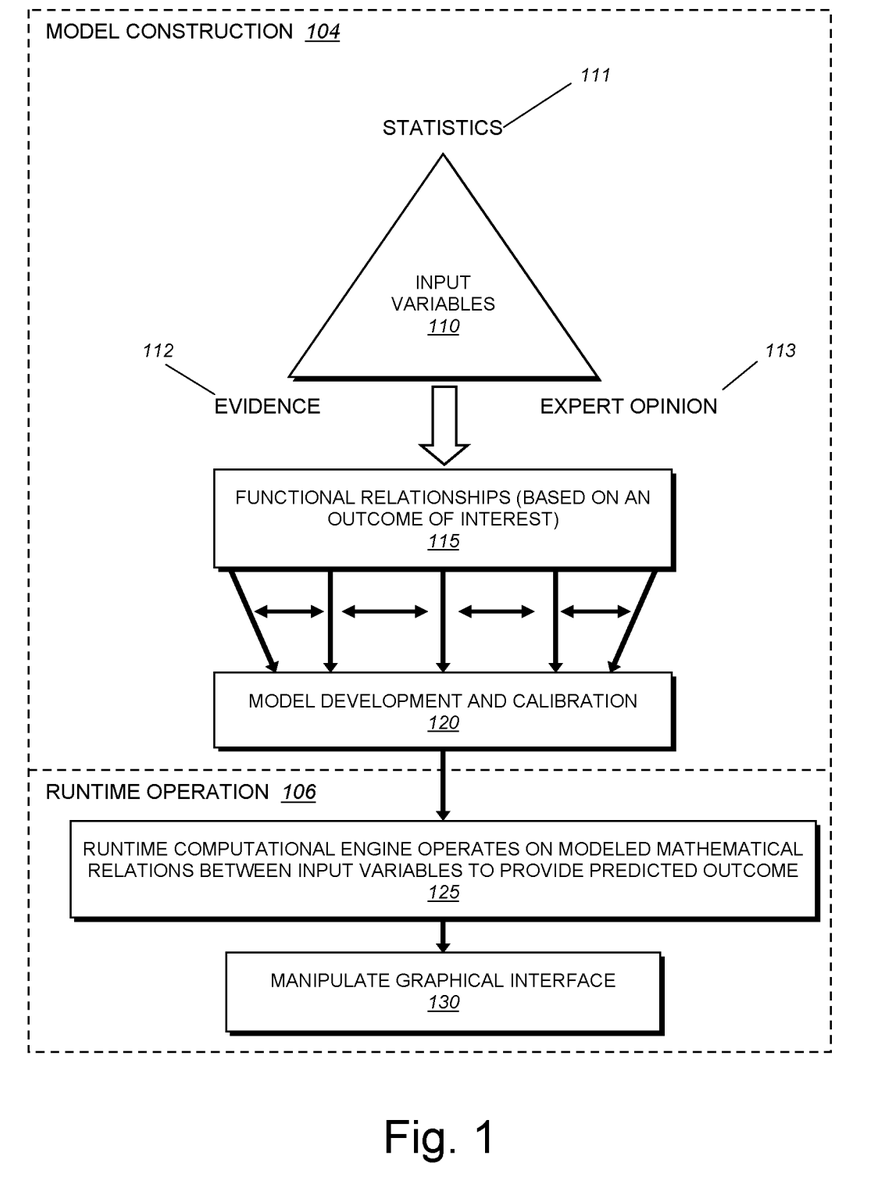
FIG. 1 is an overview block diagram for a system for communicating a predicted medical outcome of interest, according to an illustrative embodiment.
Figure 2:
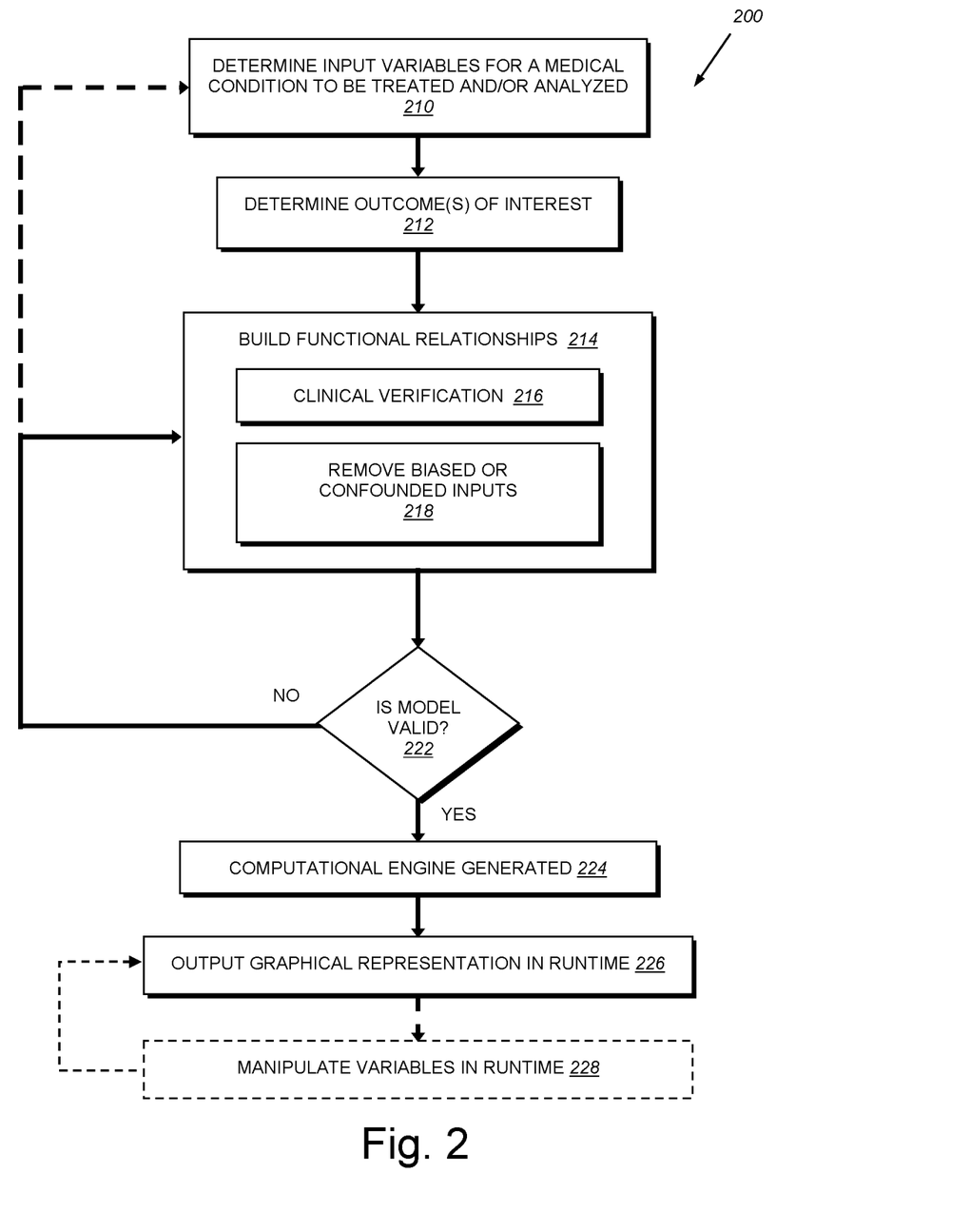
FIG. 2 is a flow chart of the procedure for communicating predicted medical outcomes, according to the illustrative embodiment.

FIG. 1 shows an overview block diagram for a system for communicating a predicted medical outcome. The system involves a model construction phase 104, in which the model is developed, and a runtime operation 106 for runtime operation of the computational engine and manipulation of input variables. The system involves a plurality of input variables 110 that are selected based on the medical condition being analyzed and/or treated. The medical condition can include, for example, analyzing a risk of a heart attack, the risk of surgery from complications due to Crohn's disease, or providing a predicted birth weight to promote healthy babies. These input variables include statistics 111, evidence 112 and expert opinion 113. The statistics 111 represent a database of raw statistical data that is gathered through standard analysis and includes a patient's age, gender, medical history, current medications, and other factors. This standard analysis is conventional to one having ordinary skill to determine the variables that are reasonably related to the medical condition and the functional relationships therebetween. The evidence 112 input variables include geo-bio-physical-chemical-based evidence, established in the medical field, and relating to a particular relationship. The input variables 110 also includes expert opinion 113, based upon research or other conventional practices in the field for acquiring variables related to an outcome of interest. Functional relationships 115 are developed based upon an outcome of interest, such as the predicted birth weight or a risk of a heart attack. The functional relationships 115 are used to develop the model of a risk of a medical condition, or a predicted medical outcome. The arrows between the functional relationship 115 and model development 120 represent the various relationships created based upon input variables, and the interrelationship therebetween that are used to generate the model. The model development and calibration 120, as described in greater detail with reference to FIG. 2, provides a model for use by the computational engine, that represents the risk of a particular condition, or the predicted medical output, for a particular outcome of interest. The model is verified by a physician or other person of ordinary skill to verify the accuracy and integrity of the model based upon know and established practice and procedure in the medical field. In the runtime operation mode 106, the developed and verified model is used for a computational engine 125 which generates the predicted outcome. The graphical interface 130 is then built by the computational engine, and provides an interactive tool for communicating and displaying the various results from manipulation of inputs or treatment options through the computational engine for an outcome of interest. As shown, the interface can be manipulated at 130, which loops back to the computational engine to produce another predicted outcome. This loop can continue so long as the input variables are manipulated.

Reference is now made to FIG. 2 detailing a procedure 200 for predicting a medical result based upon a medical condition and/or an outcome of interest. The procedure 200 is performed within a computer or similar processing system (see 830 in FIG. 8 below) and thereby predicted medical outcomes for patients by manipulating a patient's data variables.

Referring further to FIG. 2, the procedure 200 begins with step 210 by inputting the particular medical condition or illness of a patient and determining the associated input variables. The illustrative system is contemplated as a "multi-use" system, in that it is capable of analyzing and/or treating virtually any medical condition when appropriate parameters are programmed for that condition. The description details its exemplary application to Crohn's disease in FIGS. 4-7 and a predicted birth weight in FIGS. 9 and 10. However the system and method described herein is applicable to any disease or medical condition, including cancers, diabetes, heart disease, lung disease and rheumatologic diseases, among a variety of others in which the availability of predictive outcomes according to this system and method are beneficial. Because the type of medical condition is analyzed according to variables differently, the type of medical disease is indicated to improve the prediction of medical outcomes.

At step 212, the outcome(s) of interest is determined, which can be a single outcome of interest (i.e. risk of heart attack) or can include a plurality of outcomes of interest (i.e. risk of death, risk of surgery, risk of paralysis). For a plurality of medical outcomes, the various outcomes can be likewise manipulated as an input variable by the computational engine to affect the resulting graphical representation for the predicted outcome. This enhances the overall flexibility of the illustrative system and method by allowing selection of one or more outcome(s) of interest.

The procedure then employs statistical or graphical modeling to display the predicted medical outcomes. This is performed by building functional relationships at step 214 that are used to develop the model at step 220. The functional relationships at step 214 are subject to clinical verification 216, wherein a clinician or other person having ordinary skill in the medical field, verifies the relationships established by the input variables. The clinician then removes biased or confounded inputs at step 218. Biased or confounded input variables can undesirably affect the output of the model and thus need to be effectively removed to generate a valid model output. An example of confounding is a functional relationship defined as: eating ice cream causes shark attacks. This is not true, because it is the fact that in the summer people eat ice cream and the shark attacks in the summer because it is warmer out, and not because of the ice cream. An example of biased is that the administration of a drug appears to be causing complications. However it is readily recognized by clinicians and others in the medical field, that the patient already had the complication when the drug was administered, so it is biased. These recognized medical relationships are verified by a clinician or other medical personnel to build valid functional relationships.

The model is then developed at step 220. The procedure described herein employs Cox proportional analysis, along with System Dynamics Analysis, to perform the graphical modeling of predicted medical outcomes. However, any appropriate statistical or graphical modeling tools and techniques may be employed.

At procedure step 220, these data variables are input to perform an analysis, such as Cox proportional analysis. Analyzing the variables using standard Cox proportional analysis produces model input variables. These model input variables include a baseline hazard function and hazard ratios for each significant variable. The Cox proportional analysis, also known as Cox Proportional Hazards Model, is a well-known technique for determining the effects of certain variables or factors that interoperate on survival of a subject or group of subjects. By way of further background, a description of the Cox Model can be found in Cox Proportional-Hazards Regression for Survival Data, John Fox, February 2002.

A Cox proportional analysis procedure, as performed at step 220, determines a baseline hazard function and hazard ratios for each significant variable. For a particular disease, the baseline hazard function represents a hypothetical, average patient. For example, a study performed of typical patients' survival time, can provide an average value for each variable based on the average survival time of the patients.

In an illustrative embodiment, the baseline hazard function is represented as a survival curve. This baseline survival curve is changed (i.e. "flexed" up or down) by each variable, depending on the weight of each variable. Thus, the variables of each patient will alter the baseline survival curve, creating a "customized" patient-specific survival curve that maintains the same general shape as the baseline survival curve.

The Cox proportional analysis performed at step 220 also determines hazard ratios of each significant variable. As the variable values are entered into the system for each particular patient, the ratio, or relative weight, for each variable is determined.

Then, System Dynamics Analysis (SDA) is performed on the model input variables from the Cox Proportional analysis. SDA is a mathematical approach to account for the variables that interact in complex ways, affecting the medical condition, and analyzes the interaction of variables on the overall system. Computer simulations based on SDA can convey the expected outcome of a medical condition.

More particularly, SDA is performed incorporating the baseline hazard function and a hazard ratio for each significant variable. SDA is a method for understanding the behavior of complex systems over time. The method determines this dynamic behavior of a complex system by analyzing the relationships (often time-delayed) among the system components themselves. The system components in the case of SDA for medical outcomes include the variables discussed herein.

Performing SDA involves analyzing both behavior of individual components and the relationship between the components. SDA accomplishes prediction by running "what if" simulations to determine how the system should change over time. These are typically performed for a number of variables, including available medical treatments. In an illustrative embodiment, the SDA can also incorporate applicable data from medical literature. These data from relevant medical literature improves medical outcomes by considering all relevant factors.

Upon development of a model output at step 220 and model calibration, the procedure determines if the model is valid at step 222. This is performed based upon known established practice in the medical field pertaining to the outcome of interest. If the model is not valid at step 222, the clinician or physician can return (solid arrow) to step 214 to verify the functional relationships, or can return (dashed arrow) to step 210 to verify the input variables. This comprises conventional verification of functional relationships, known to those of ordinary skill.

A valid model from step 222 is used as the computational engine at step 224. The predicted outcome generated by the computational engine is output as a graphical representation at step 226. This graphical representation can include a graphical display of the risk of complication over time, without medical treatment, or a predicted medical output based upon an outcome of interest. This graph shows the customized, patient-specific survival curve, with no medical treatment applied as a variable in determining the risk of complication. A medical treatment can be applied by the computational engine to thereby display the survival curve with a particular medical treatment applied.

Once a graphical representation is output at step 226, one of a plurality of treatment options can be input to the system. These treatment options vary depending on the particular medical condition that is being analyzed. For example, as shown in greater detail with reference to FIG. 4, some available treatment options for treating Crohn's disease include prednisone, immunomodulators, anti-tumor necrosis factor agents, and natalizumab.

In a runtime operation, a user employs the model for the computational engine and selects one of the treatment options (manipulating the variables 228) via a user interface associated with the computer executing the procedure 200. The computational engine determines the risk of complication of the medical condition with the selected treatment, or other appropriate variables manipulated, as shown in the dashed method step 228. The variables manipulate the graphical representation (dashed arrow 230) to produce the graphical representation of step 226. A user can manipulate the variables to provide a new graphical representation at step 228. The variables can be manipulated (step 228 repeated) for each available treatment and/or changing factor, to assist in determining the predicted outcome.

Figure 3:
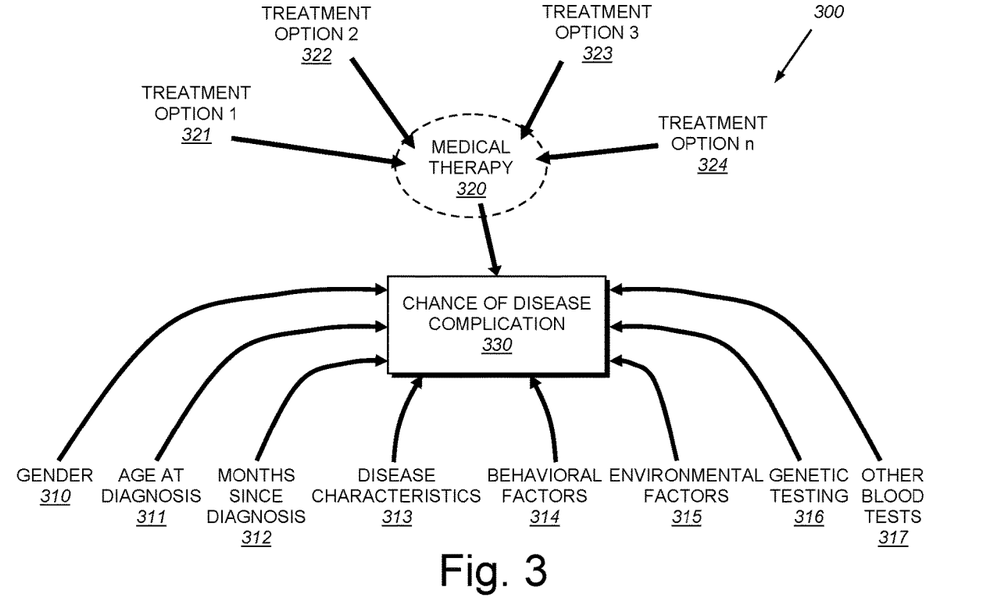
FIG. 3 is an overview of a generic disease model structure according to the illustrative embodiment.

FIG. 3 details an overview of a generic model structure 300. The generic model structure 300 predicts medical outcomes based on interactions between variables that influence complications and the effect of medical therapy. FIG. 3 shows a generic model for the computational engine that is generally applicable for any disease having known variables that influence complications of a medical condition. For a disease-specific model structure, see alternatively FIG. 4 and the corresponding description below, and the application of the model structure to Crohn's disease.

The generic disease model 300 provides a computational engine to predict outcomes for a medical condition based on interactions between variables 310-317 and the effect of medical therapy 320. As shown, the plurality of variables include the patient's gender 310, age at diagnosis 311, number of months since diagnosis 312, disease characteristics 313, behavioral factors 314, environmental factors 315, genetic testing 316 and other blood tests 317. These variables are exemplary and not demonstrative of an exhaustive list of all possible variables that influence the chance of disease complication 330.

A medical therapy or treatment 320 is then selected, either treatment option1 321, treatment option2 322, treatment option3 323 or treatment option4 324. These treatment options vary depending on the particular medical condition that is being analyzed. The treatment that is selected also affects the chance of disease complication, as some treatments are more effective than others. Together, the variables entered into the system, and the medical treatment selected, determine the chance of disease complication.

Each variable has its own switch that is easily manipulated by the computational engine to alter the value of the variable as different patients are analyzed. Each medical treatment also has its own toggle switch, so that the survival curve for each medical treatment, or a plurality of medical treatments combined, can be readily viewed by healthcare professionals and also patients. The specific number, layout and information associated with each switch are provided by the model for the disease being programmed to the computer. The scale and granularity of data altered by moving each toggle can be varied depending on the significance of incremental differences in such data to the model (i.e. some data can be finely varied while other data is of the on/off variety).

The model for the computational engine can be developed using, for example, Vensim simulation software available by Ventana Systems, Inc. of Harvard, Mass., Stella by isee systems, inc. of Lebanon, N.H., or PowerSim, a Norwegian company.

Figure 4:
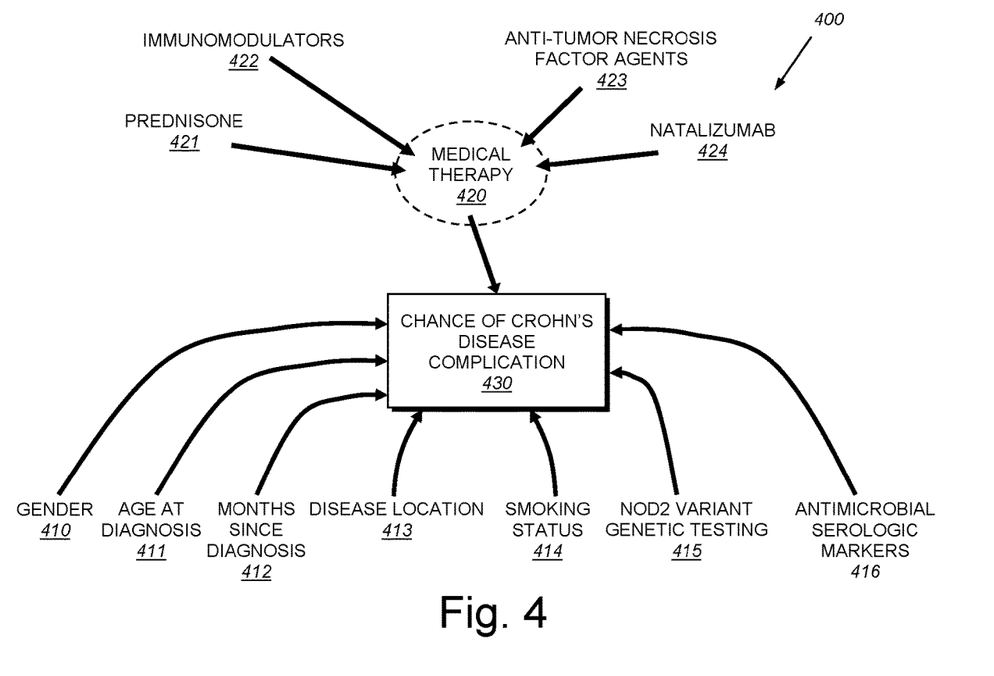
FIG. 4 is an overview of a Crohn's disease-specific model structure, according to an illustrative embodiment.

A disease-specific model structure 400 is illustrated in FIG. 4, similar to that shown in FIG. 3, however disease specific to Crohn's disease. For patients with Crohn's disease, certain variables have been identified that influence the chance of a disease related complication (such as requiring a surgery). Operationally significant variables include: individual patient characteristics (gender 410 and age 411); time since diagnosis of Crohn's disease 412; location of disease 413, including extent of bowel involvement (i.e. stomach, small bowel, colon); smoking status 414; NOD2 genetic variants 415 and antibodies to serologic microbial antigens 416.

Various treatments are available as medical therapy 420, each differently affecting the chance of Crohn's disease complication 430. Medications known to influence the chance of a complication include: prednisone 421; immunomodulators 422 (azathioprine and 6-mercaptopurine); anti-tumor necrosis factor (TNF) agents 423 (infliximab, adalimumab, certolizumab pegol); and natalizumab 424. As new factors are identified, they can be readily incorporated to update the model.

The different variables and medical treatments affect the chance of Crohn's disease complication 430. The chance of disease complication 430 can thus be provided in the form of a graphical display. This allows a patient to more easily visualize and comprehend the affects of each medical treatment (or the effect of no medical treatment at all).

Figure 5:
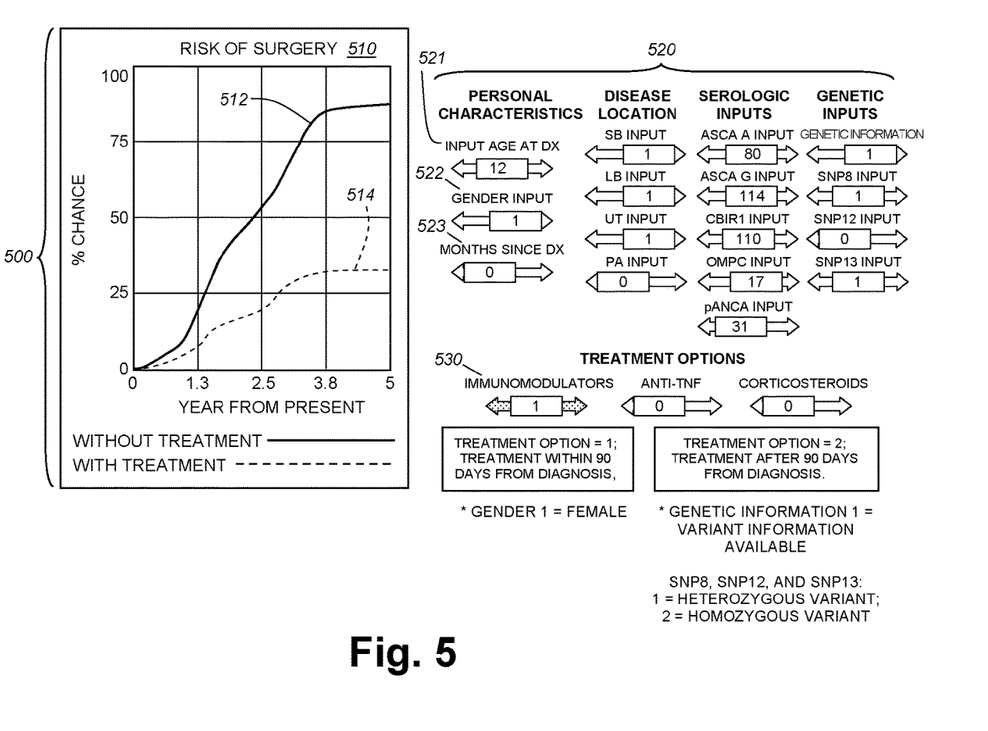
FIG. 5 shows a screenshot of a graphical user interface showing the predicted medical outcome in a patient having an increased risk of complicating without treatment, as well as a risk with a first medical treatment, according to an illustrative embodiment.
Figure 6:
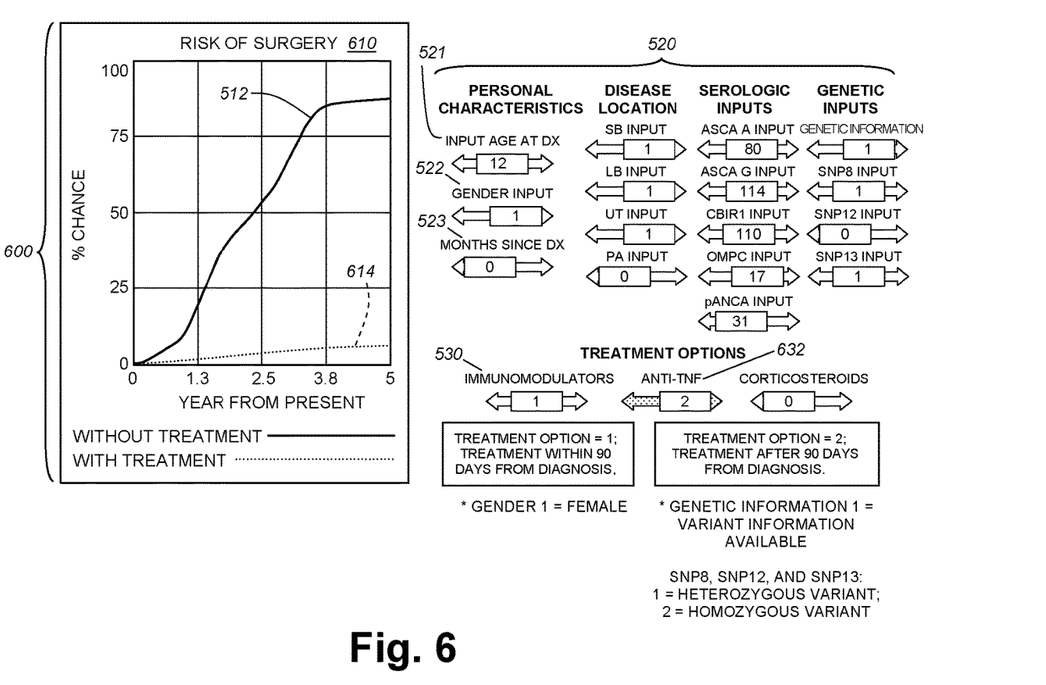
FIG. 6 shows a screenshot of the graphical user interface of FIG. 5, showing the risk of complication without treatment, as well as a risk of complication with a second medical treatment, according to an illustrative embodiment.
Figure 7:
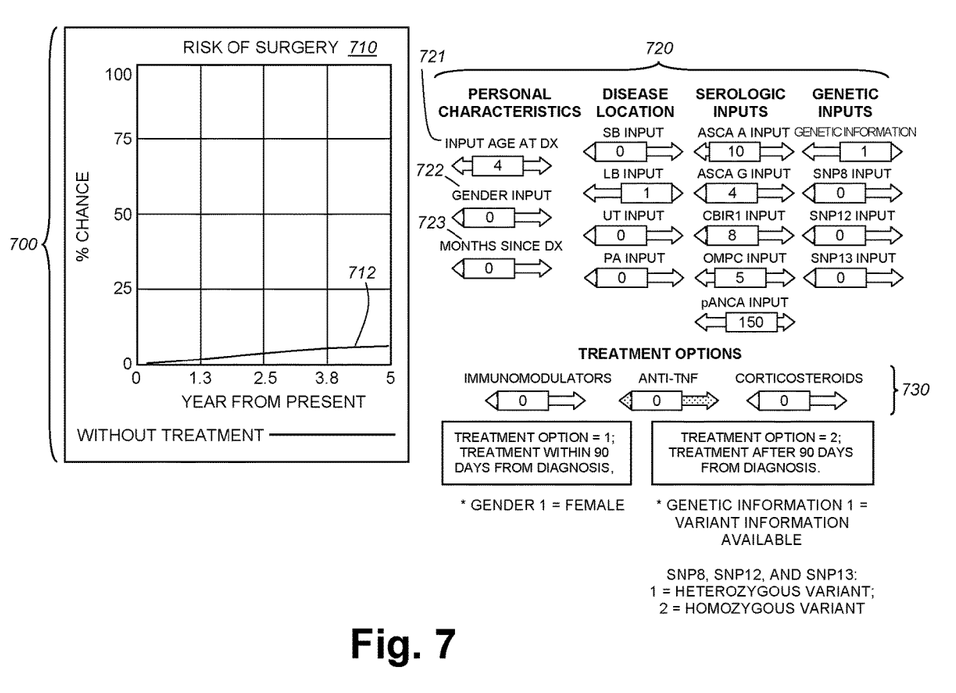
FIG. 7 shows a screenshot of a graphical user interface showing the predicted medical outcome for a patient having a decreased risk of complication, according to an illustrative embodiment.
Figure 8:
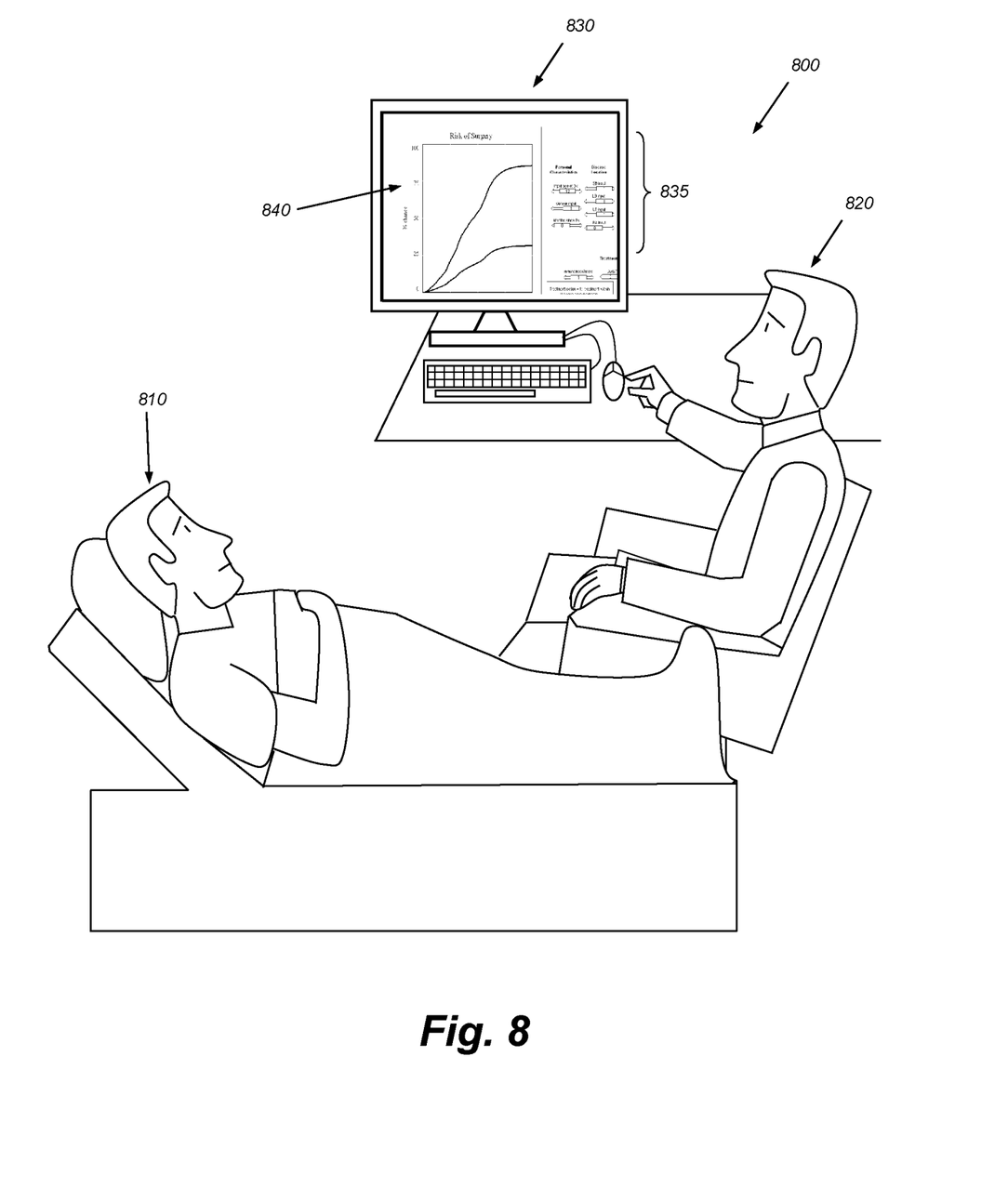
FIG. 8 shows the overall system for communicating the predicted medical outcomes to patients using System Dynamics Analysis, according to the illustrative embodiment.

Shown in FIGS. 5-8, the resulting image is of a predicted medical outcome, generated by the computational engine. If a patient has an increased risk of complication, the patient next should contemplate which medical treatment to undergo. Accordingly, as shown in FIGS. 5, 6 and 8, and described in greater detail below, the risk of complication for each medical treatment can also be displayed in a graphical manner clearly understandable to the average lay patient. This accordingly facilitates determining which medical treatment is desirable and provides patient with greater insight into the effects of each medical treatment available for the medical condition.

FIG. 5 shows a screenshot 500 of a graphical display interface projected by the computational engine employed herein, showing the graphical output image 510 and the various input variables, collectively 520, that determine the risk of complication from the medical condition. More particularly, FIG. 5 represents the chance of a need for eventual surgery for a particular exemplary patient—in this example a 12 year old female, afflicted by Crohn's disease. As indicated by the solid-line survival curve 512, there exists a high risk of needed surgery with this particular patient As discussed generally above, each variable is represented on the graphical user interface by a toggle switch. For example, toggle switch 521 represents the input age at diagnosis (Dx), which in FIG. 5 is age 12. Also, toggle switch 522 represents the gender of the patient, where 0 represents a male and 1 represents a female. Also, there is toggle switch 523, for inputting the number of months since an initial diagnosis. Each variable has a respective toggle switch, as well as each treatment, to readily input variables and display a survival curve. While sliding bars are illustrated as the switches representative of the input variables and/or treatments, any graphical representation can be employed that allows for manipulation of the variables, and should be readily apparent to those of ordinary skill. These can include slides, buttons, or a data entry text box.

The treatment selected for this exemplary scenario is immunomodulator treatment, initiated within the first 30 days of diagnosis (note the immunomodulator toggle switch 530 is set to 1), the chance of surgery is drastically decreased.

The exemplary dashed-line survival curve 514 shows the decreased risk of surgery if the patient has a first treatment (immunomodulator treatment) according to the illustrative embodiment. The input variables 520 are represented in the graphical user interface as toggle switches. They can each be varied as desired for each patient to show a multitude of possible predicted outcomes.

FIG. 6 is an exemplary screenshot 600 of a graphical display interface showing the graphical output image 610 and the various input variables, collectively 520, including a second treatment option selected for the patient. As shown, the patient has a risk of surgery as shown by the solid-line survival curve 512 is the same, without treatment. The risk of complication with the second treatment option, shown by the dashed line 614, is significantly lower than both the risk without any treatment and the risk of the first treatment, as shown in FIG. 5.

The treatment shown in FIG. 6 is another available treatment for Crohn's disease, anti-TNF therapy, started at least 90 days after diagnosis, and used in combination with immunomodulator therapy that had been started within 30 days of diagnosis (note treatment option 530 remains at '1' and anti-TNF switch 632 is now at '2'). As shown, this treatment significantly decreases the risk of complication for a patient.

FIG. 7 is an exemplary screenshot 700 of a graphical display interface employed by the computer system herein, showing the graphical output image 710 for another, second patient, according to the illustrative embodiment. As shown, the line 712 shows that this patient has a low risk of complication with his medical treatment. The input variables, collectively 720, are set to represent the particular patient to be analyzed. These include age at diagnosis (Dx) 721, which is four (4) for this patient. Variable 722 is the gender input and variable 723 is the number of months since diagnosis, shown as zero. As shown by line 712, the patient has a low risk without a medical treatment.

Accordingly, there is no need in this example for this patient to undergo medical treatment with immunomodulators or anti-TNF drugs. Thus, each of the toggle switches for treatment options 730 is set to '0' by the healthcare practitioner. While it is entirely possible to view the risk of complication with a particular medical treatment, it is not necessary where the risk of complication is so low.

FIG. 8 shows an overall system 800 for communicating predicted medical outcomes to patients. This is generally performed by a computational engine or other processing system performing the proportional and/or statistical analysis to generate a graphical representation of a medical output. The system provides a patient 810 and/or physician 820 with the opportunity to view the risk of complication of a medical disease, both with and without treatment (if treatment is desired).

This provides a physician/clinician with a visual graph of the risk of complication of the disease that can be easily communicated to patients or used for the physician's own resources. The various graphs can be created for each medical treatment available. Healthcare providers are thus able to more effectively communicate the risks associated with each medical treatment or affect a particular variable has on a patient. Also, the patient is able to make informed choices with respect to the treatment options and their own behavior. Although a single physician or clinician 820 is illustrated, this can be replaced with a group of consulting physicians to determine predicted medical outcomes.

To obtain the risk of complication, a healthcare provider 820 inputs the data variables into the computer 830. These variables are readily interchangeable by manipulating toggle switches 835, as discussed generally above. This results in the display graph 840 showing both the risk of complication without treatment, and the risk of complication if the patient undergoes the medical treatment proposed, as determined by the computational engine.

This graphical display can be saved by the healthcare provider or patient, and can also be printed so that all interested parties have a copy and an opportunity to view the results. This representation, thus, allows patients an opportunity to readily view, in an easily discernable graphical display format, the risk of complication for a plurality of available treatment options. This gives patients the opportunity to review their options with their families and have a visual representation of these treatment options and the potential benefits.

Figure 9:
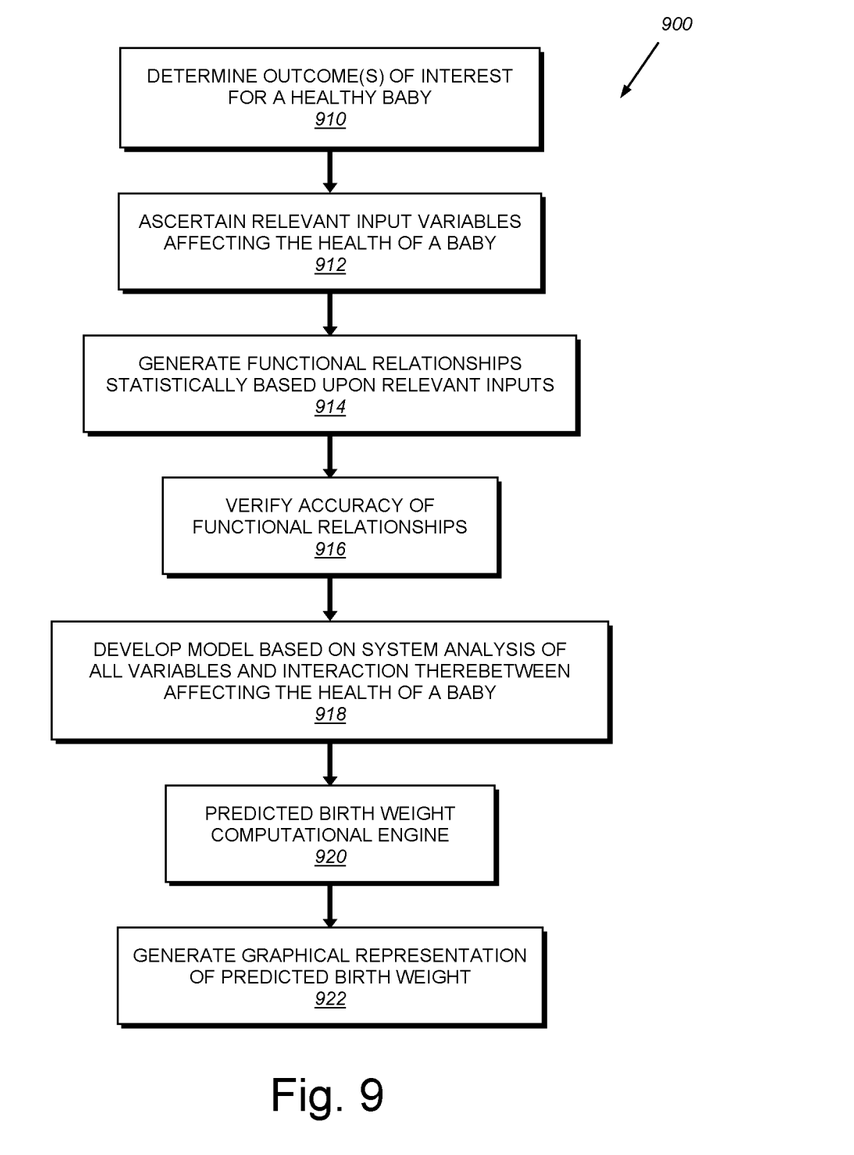
FIG. 9 shows a flow chart of the procedure for communicating a predicted birth weight for a healthy baby, in accordance with an illustrative embodiment.
Figure 10:
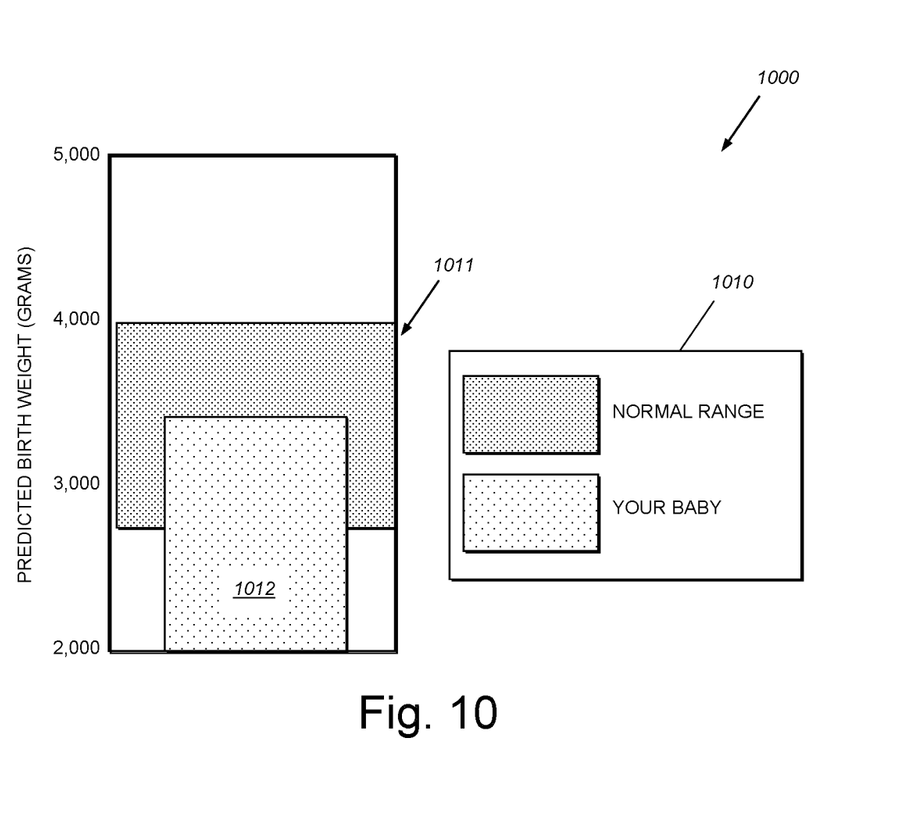
FIG. 10 shows an exemplary screen display of a graphical user interface showing the predicted birth weight for a baby, in accordance with the illustrative embodiment.

Having now described the general applicability of the teachings herein to a heart attack risk, and complications resulting from Crohn's disease, reference is made to FIGS. 9 and 10 showing a procedure flow chart and exemplary screen shot, respectively, for predicting the birth weight of a baby. Reference is made to FIG. 9 showing a procedure

900 for communicating a predicted birth weight to a patient or physician. The procedure 900 begins by determining an outcome of interest for a healthy baby 910, which is the predicted birth weight of a baby, according to the illustrative embodiment. The outcome of interest can include the predicted birth weight, or the risk of the baby developing a certain condition at birth. At step 912 the relevant input variables affecting the health of a baby are ascertained. These include the mother smoking, drinking, taking prenatal vitamins, age, and other factors (medically based) reasonably affecting the birth weight of a baby. These are used to generate functional relationships at step 914. For example, a functional relationship is that smoking decreases the birth weight, or that taking prenatal vitamins increases birth weight. The accuracy of the functional relationships are verified at step 916 based upon established practice in the medical field. This can be performed by a clinician, physician, or any other person having ordinary skill. For example, a functional relationship from standard analysis could appear to indicate that sleeping more causes an increased birth weight. However, a physician would recognized that the sleeping is confounded by the fact that larger women sleep more, and thus the larger size of the mother contributes to the larger size of the baby. These factors are removed by the physician or clinician to develop a precise model.

The model is then developed based upon a system analysis of all variables and interaction therebetween affecting the health of a baby at step 918. This can be performed using System Dynamics Analysis (SDA) or any system analysis approach that incorporates all relationships (variables and functional relationships) to build a system model for the computational engine. It is noted that the steps of FIG. 9 can be performed in any order to carry out the invention and provide a precise predicted medical outcome.

At step 920 the predicted birth weight computational engine is generated based on the verified model. A clinician or physician verifies the model prior to being used as the computational engine to ensure that the model appropriately reflects the functional relationships and input variables affecting the outcome of interest. A graphical representation of predicted birth weight is generated at step 922 by the computational engine. A graphical representation, for example resulting from step 922, is shown in the exemplary screen shot 1000 of FIG. 10. As shown in the key 1010, a normal range 1011 for baby weight is shown, as well as the predicted birth weight 1012. This allows a patient or physician to readily view the predicted birth weight based upon the various input variables.

The advantages of the illustrative system and procedure should be readily apparent to one of ordinary skill. It is recognizes that the system and method is readily applicable to a limitless number of medical conditions, ranging from pregnancy to heart attack, Crohn's disease to Rheumatoid Arthritis. The inputs of the system are also highly variable, and cover any factor or treatment that reasonably affects a medical outcome.

The foregoing has been a detailed description of illustrative embodiments of the invention. Various modifications and additions can be made without departing from the spirit and scope of this invention. Each of the various embodiments described above can be combined with other described embodiments in order to provide multiple features. Furthermore, while the foregoing describes a number of separate embodiments of the system and method of the present invention, what has been described herein is merely illustrative of the application of the principles of the present invention. For example, the computational engine described herein can be any custom built or already existing computational engine that operates on a plurality of input variables and the interrelationships to compute and display a predicted outcome. Also, the system and method herein has been described with the example of Crohn's disease, however is highly applicable to all disease having know variables that affect the outcome of the disease. Also, the graphical user interface displays are only shown by way of example of possible layouts for the features and advantages of the illustrative embodiments. However, they are not meant to illustrate precise requirements for displays, but only as a means to provide possible screens to implement the procedures discussed herein. Furthermore, the procedure utilizes Cox proportional analysis and System Dynamic Analysis to create the graphical outputs. Nevertheless, it is expressly contemplated that any appropriate statistical or graphical modeling technique can be employed that creates a graphical output of predicted medical outcomes. In addition, any of the procedures described herein can be implemented as hardware, software consisting of a computer-readable medium containing program instructions or a combination of hardware and software. Likewise identifiers for the various variables can be interchanged without departing from the scope of this invention. It is expressly contemplated that any or all of the processes and data structures described above can be implemented in hardware, software or a combination thereof. A software implementation may comprise a computer-readable medium containing executable program instructions for execution on a computer. Accordingly, this description is meant to be taken only by way of example, and not to otherwise limit the scope of this invention.

What is claimed is:

1. A system for communicating a predicted outcome for a medical condition in a medical field, the system comprising:
a computational engine running on a computer that analyzes each of a plurality of input variables, each corresponding to the medical condition, and constructed and arranged to be manipulable so as to affect the predicted outcome, by performing a Cox Proportional analysis on the plurality of input variables to generate a hazard ratio for each of the plurality of input variables and a baseline hazard function, the hazard ratio comprising a weight for each of the plurality of input variables, and then performing system dynamics analysis by incorporating the hazard ratio for each of the plurality of input variables and the baseline hazard function, the system dynamics analysis analyzing one or more time-delayed relationships, from a present time to a predetermined future time, among the hazard ratio for each of the plurality of input variables and the baseline hazard function exhibiting a non-linear dynamic behavior between the present time and the predetermined future time and incorporating data from medical literature, to develop a model, wherein the model is subsequently validated based upon statistically validated functional relationships, known clinical practice and prior evidence in the medical field to provide a validated system model that determines the predicted outcome; and
a display that displays a graphical representation of the one or more time-delayed relationships generated by the computational engine that provides the predicted outcome as a non-linear dynamic representation as a function of time from the present time to the predetermined future time.

2. The system as set forth in claim 1 wherein the input variables are molded based upon statistical data, evidential data and expert opinion.

3. The system as set forth in claim 2 further comprising a database in which the statistical data is stored.

4. The system as set forth in claim 1 wherein some of the plurality of input variables includes a treatment option for the medical condition.

5. The system as set forth in claim 1 wherein at least one of the plurality of input variables comprises a desired outcome such that the graphical representation displays the predicted outcome affected by the desired outcome.

6. The system as set forth in claim 1 wherein the predicted outcome is a risk of having a heart attack.

7. The system as set forth in claim 1 wherein the predicted outcome is a risk of complications from Crohn's disease.

8. The system as set forth in claim 1 wherein the predicted outcome is a predicted birth weight for a baby.

9. A method for determining a predicted medical outcome, the method comprising the steps of:
- determining an outcome of interest for a medical condition;
- selecting input variables associated with the medical condition; and
- developing, using a computer, a computational engine that analyzes each of the input variables by:
  (i) performing a Cox Proportional analysis on the plurality of input variables to generate a hazard ratio for each of the plurality of input variables and a baseline hazard function, the hazard ratio comprising a weight for each of the plurality of input variables, and then
  (ii) performing system dynamics analysis by incorporating the hazard ratio for each of the plurality of input variables and the baseline hazard function, the systems dynamic analysis analyzing one or more time-delayed relationships, from a present time to a predetermined future time, among the hazard ratio for each of the plurality of input variables and the baseline hazard function exhibiting a non-linear dynamic behavior between the present time and the predetermined future time and incorporating data from medical literature, to develop a model
  (iii) subsequent to (ii), validating the model based upon statistically validated functional relationships, known clinical practice and prior evidence in the medical field to provide a validated system model that determines the predicted medical outcome; and
- generating a graphical representation of the one or more time-delayed relationships generated by the computational engine, that provides the predicted outcome as a non-linear dynamic representation as a function of time from the present time to the predetermined future time.

10. The method as set forth in claim 9 further comprising: generating a graphical user interface representing the predicted medical outcome.

11. The method as set forth in claim 10 further comprising manipulating the input variables to provide a second outcome of interest.

12. A graphical user interface (GUI) for a display for communicating a predicted medical outcome in a medical field, the GUI comprising:
- a plurality of switches on the GUI on the display, each associated with one of a plurality of variables corresponding to the predicted medical outcome, and constructed and arranged to be manipulable so as to modify each of the plurality of variables to affect the predicted medical outcome;
- a screen portion on the GUI on the display, that displays the predicted medical outcome; and
- wherein the predicted medical outcome is determined by a computational engine running on a computer that analyzes each of the plurality of variables by performing a Cox Proportional analysis on the plurality of input variables to generate a hazard ratio for each of the plurality of input variables and a baseline hazard function, the hazard ratio comprising a weight for each of the plurality of input variables, and then performing system dynamics analysis by incorporating the hazard ratio for each of the plurality of input variables and the baseline hazard function, the system dynamics analysis analyzing one or more time-delayed relationships, from a present time to a predetermined future time, among the hazard ratio for each of the plurality of input variables and the baseline hazard function exhibiting a non-linear dynamic behavior between the present time and the predetermined future time and incorporating data from medical literature, to develop a model, wherein the model is subsequently validated based upon statistically validated functional relationships, known clinical practice and prior evidence in the medical field to provide a validated system model that the computational engine uses to determine the predicted medical outcome; and
- a graphical representation of the one or more time-delayed relationships generated by the computational engine, that provides the predicted outcome as a non-linear dynamic representation as a function of time from the present time to the predetermined future time.

13. The GUI set forth in claim 12 wherein the predicted medical outcome is displayed as a line graph representative of both a with-treatment predicted outcome and a without-treatment predicted outcome.

14. The GUI as set forth in claim 12 wherein the predicted medical outcome is displayed as a bar graph representative of the predicted outcome.

15. The GUI as set forth in claim 12 wherein the predicted medical outcome is displayed as a spreadsheet file with downloadable data.

16. The GUI as set forth in claim 12 wherein predicted medical outcome is displayed as a graph showing relative values versus a scale.

* * * * *